United States Patent
Nagaishi et al.

[11] Patent Number: 6,084,399
[45] Date of Patent: Jul. 4, 2000

[54] METHOD AND APPARATUS FOR DETERMINING CONCENTRATION OF MAGNETIC SUBSTANCES IN A NON-MAGNETIC SUBSTANCE USING A SQUID

[75] Inventors: Tatsuoki Nagaishi; Hideo Itozaki, both of Itami, Japan

[73] Assignee: Sumitomo Electric Industries, Ltd., Osaka, Japan

[21] Appl. No.: 09/048,059

[22] Filed: Mar. 26, 1998

[30] Foreign Application Priority Data

Mar. 26, 1997 [JP] Japan ................... 9-091736

[51] Int. Cl.[7] .............. G01R 33/12; G01R 33/035; G01N 27/74; G01N 27/82
[52] U.S. Cl. ............ 324/204; 324/239; 23/61.42
[58] Field of Search .................. 324/204, 239, 324/240, 248, 235; 73/53.07, 61.42; 399/63; 118/689

[56] References Cited

U.S. PATENT DOCUMENTS

| | | | |
|---|---|---|---|
| 4,243,059 | 1/1981 | Hammon et al. ............ | 324/204 |
| 5,305,751 | 4/1994 | Chopp et al. ............... | 128/654 |

FOREIGN PATENT DOCUMENTS

| | | |
|---|---|---|
| 0 634 652 | 1/1995 | European Pat. Off. . |
| 0 667 525 | 8/1995 | European Pat. Off. . |
| 195 10 114 | 9/1996 | Germany . |
| 6-204068 | 7/1994 | Japan . |
| 7-5137 | 1/1995 | Japan . |
| 7-260912 | 10/1995 | Japan . |
| 2 253 061 | 8/1992 | United Kingdom . |

OTHER PUBLICATIONS

Research Disclosure, XP–002069897 pp. 441 (1986).
Derwent Publication, XP–002069898 (No Date).
Patent Abstract of Japan, 03 073824 (1991).
Patent Abstract of Japan, 60 006850 (1985).
Cochran, "Squids for NDT; The Technology and its Capabilities" *British Journal of Non–Destructive Testing* 35:173–182 (1993).

*Primary Examiner*—Walter E. Snow
*Attorney, Agent, or Firm*—Foley & Lardner

[57] ABSTRACT

Method and apparatus for determining concentration of a trace of contaminant magnetic substances contained in a non-magnetic substance. A magnetic field (3) is applied to the non-magnetic substance (1) from outside a duct (2) through which the non-magnetic substance is advanced so that magnetic substances contained in the non-magnetic substance are magnetized. At a downstream in the duct, an intensity of magnetic field produced substantially only by the magnetized magnetic substance is detected by a magnetic sensor (8) having a superconducting quantum interference device (SQUID).

8 Claims, 5 Drawing Sheets

METHOD AND APPARATUS FOR DETERMINING CONCENTRATION OF MAGNETIC SUBSTANCES IN A NON-MAGNETIC SUBSTANCE USING A SQUID

BACKGROUND OF THE INVENTION

1. Field of the Invention

The present invention relates to density measurement of magnetic substances, in particular to a method and apparatus for determining concentration of a trace of contaminant magnetic substances suspended or contained in a non-magnetic substance by a superconducting quantum interference device (SQUID).

2. Description of the Related Art

FIG. 1 is a flow diagram illustrating a process for producing ceramic articles in which material powders purchased on market are subjected to a variety of severe examinations to check their qualities. In practice, the material powders are dispersed in water or alcohol to prepare a slurry in the step A. In the step B, the slurry is stirred, for example by a propeller type stirrer to prepare finer powders. Water or alcohol is evaporated in the step C by so-called spray-dry technique to obtain a conditioned powder which can be used in subsequent steps including molding or shaping (D), preliminary sintering (E) and final sintering (F) to obtain a desired final product of ceramics.

Material ceramic powders contains magnetic substances such as iron and nickel as impurities. Magnetic substance such as iron is often introduced in their manufacturing process for example in a form of solid solution in the material powders. In fact, powder of silicon nitride available on market contain iron as an impurity. This fact is described in a purity analysis table attached to commercially available powders.

The content of magnetic substance such as iron in material powders which exist microscopically in grain boundary or in grain itself is very low of ppm order but must be known or evaluated precisely so as to control the quality of ceramic products. In practice, it is necessary to know precise content of magnetic substances such as iron contained in material powders at as an earlier stage as possible, preferably before the dispersion stage B in the production process by measuring the density of magnetic fluid at high precision for example.

In a process for treating metal powders such as aluminum powder, iron is an undesirous contaminant impurity. Therefore, in this case also, it is requested to determine the density of magnetic fluid at high precision to know the precise content of magnetic substance such as iron contained in material powders.

Heretofore, the density (content) of magnetic elements such as iron contained in non-magnetic substances or material powders as contaminant impurities has been determined mainly by chemical analysis in which objective magnetic substances are extracted firstly and are determined by Inductively Coupled Plasma-atomic Emission Spectroscopy or by chemical analysis. In any ways, objective substance is dissolved firstly in a solution to determine the density of magnetic substances.

This conventional destructive analysis system, however, requires sophisticated procedure including sampling work of the objective substance followed by pre-treatment for analysis, so that it takes at least several hours to analysis and analysis can not be effected continuously.

Non-destructive analysis system is already known to determine physical value correlated to magnetic material which is contained at relatively high concentration or proportion in a liquid substance. Japanese patent publication No. JP-A-6-204,068 discloses an apparatus for determining easily and rapidly the water content in a magnetic material in a slurry form of oxide powder on line.

JP-A-7-5,137 discloses an apparatus for trapping iron particles magnetically in a circulating fluid and JP-A-7-260, 912 discloses a technique to determine the density of saturated magnetic flux by means of a permanent magnet and two sample holders. In these patents, physical values correlated to relatively high concentration or proportion of magnetic component such as iron particles or iron powder are determined.

In these known techniques in which magnetic properties which magnetic material or iron powder possess are utilized, relatively strong magnetic force of magnetic material or iron powder itself is detected by a coil or by means of hall effect device in a form of inductance change. Sensitivity of these detectors, however, can not be increased to higher levels because too sensitive pulse-like response from individual magnetic particles disturb measurement of objective substance, so that these techniques can not be used to determine the concentration of a trace of contaminant magnetic substances dispersed uniformly in a non-magnetic substance.

In fact, chemical analysis has been only means that can be used to determine the precise concentration of a trace of magnetic substance contained in a non-magnetic substance.

An object of the present invention is to provide non-destructive method and apparatus for determining the density of a trace of magnetic substance such as iron contained in a non-magnetic substance by using a superconducting quantum interference device (SQUID) as a magnetic sensor at high precision and in non-contacted mode.

Another object of the present invention is to provide method and apparatus for measuring continuously the density of magnetic substance, which can be used in a variety of production processes as a monitor.

Still another object of the present invention is to provide a measuring method and apparatus of the density of magnetic substance, which can be operated in line without delay.

SUMMARY OF THE INVENTION

The objects can be achieved by the present invention in which magnetic substances in a nonmagnetic substance to be analyzed are magnetized under a predetermined magnetic field and an intensity of magnetic field which is proportional to the density of the magnetized magnetic substance is measured by a magnetic sensor of high sensitivity under no influence of outside magnetic noise such as terrestrial magnetism. The magnetic sensor has a superconducting quantum interference device (SQUID) and the density of magnetic substances can be determined immediately on line from a calibration curve which is prepared previously from a relationship between the density of magnetic substance and output of the magnetic sensor without contacting with the substance to be analyzed.

Now, the present invention will be described with reference to attached drawings which show embodiments of the invention but does not limit the scope of the invention.

In the present invention which can be used to evaluate the concentration of a trace of a variety of contaminant magnetic substances such as iron contained in a non-magnetic substance, the substance to be analyzed is changed in a fluid form of fine powder or liquid so that measurement can be effected continuously.

Figure 1:
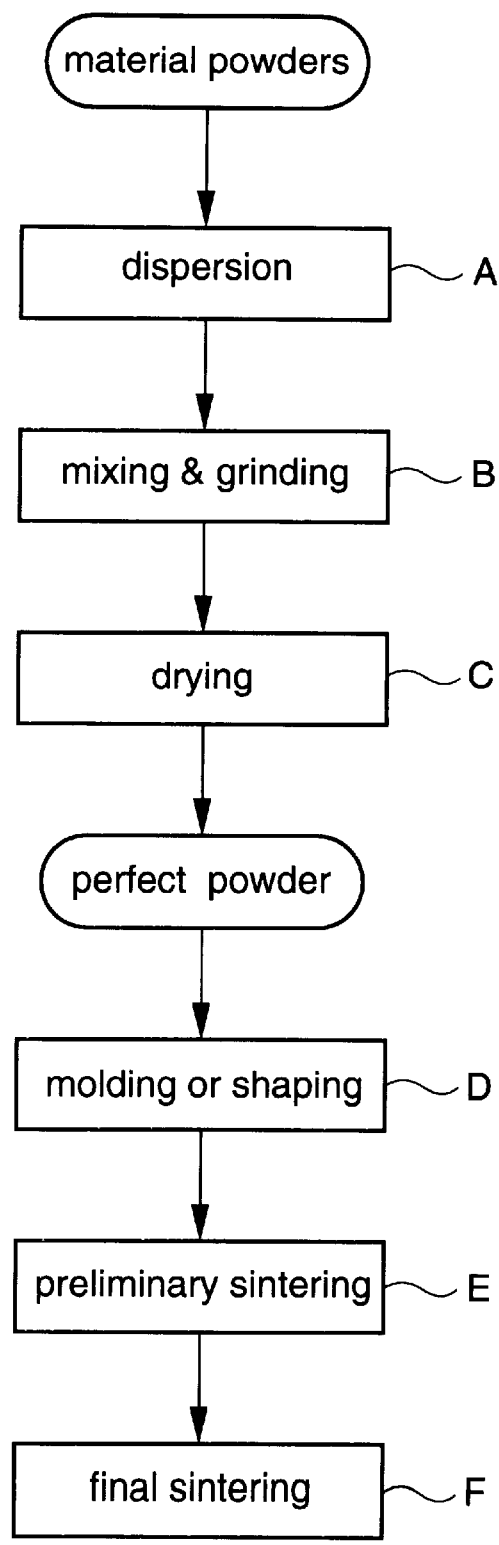
FIG. 1 is a flow diagram illustrating a process for producing ceramic articles, to which the present invention is applicable.

For example, in a process shown in FIG. 1, material powder or its finely divided powder is dispersed in a liquid such as water or alcohol. The method according to the present invention can be added to or inserted in a continuous production process before or after the dispersion stage A or the mixing and grinding stage B. The method according to the present invention is effected preferably at as early stage as possible for example before or after the dispersion stage A so as to determine precise density of magnetic elements in material powder, since there is such a danger that iron is introduced from worn stirrer used in the mixing and grinding stage B. When the method according to the present invention is effected during a first half stage of the dispersion stage A, the method according to the present invention can be inserted as one stage in a continuous production process between the stages A and B to determine the density of magnetic elements in material powder precisely. High concentration of magnetic substances such as iron introduced by worn stirrer in the mixing and grinding stage B is preferably detected by any suitable method other than the present invention.

The technique according to the present invention is applicable also to other material powder of metal powders such as aluminum powder to evaluate the density of a trace of magnetic elements such iron contained therein.

The method according to the present invention can be effected on line in actual production process without sampling work for example between the stages A and B or between the stages B and C so that measurement can be carried out continuously and hence the method according to the present invention can be used as a monitoring technique in actual production lines.

Figure 2:
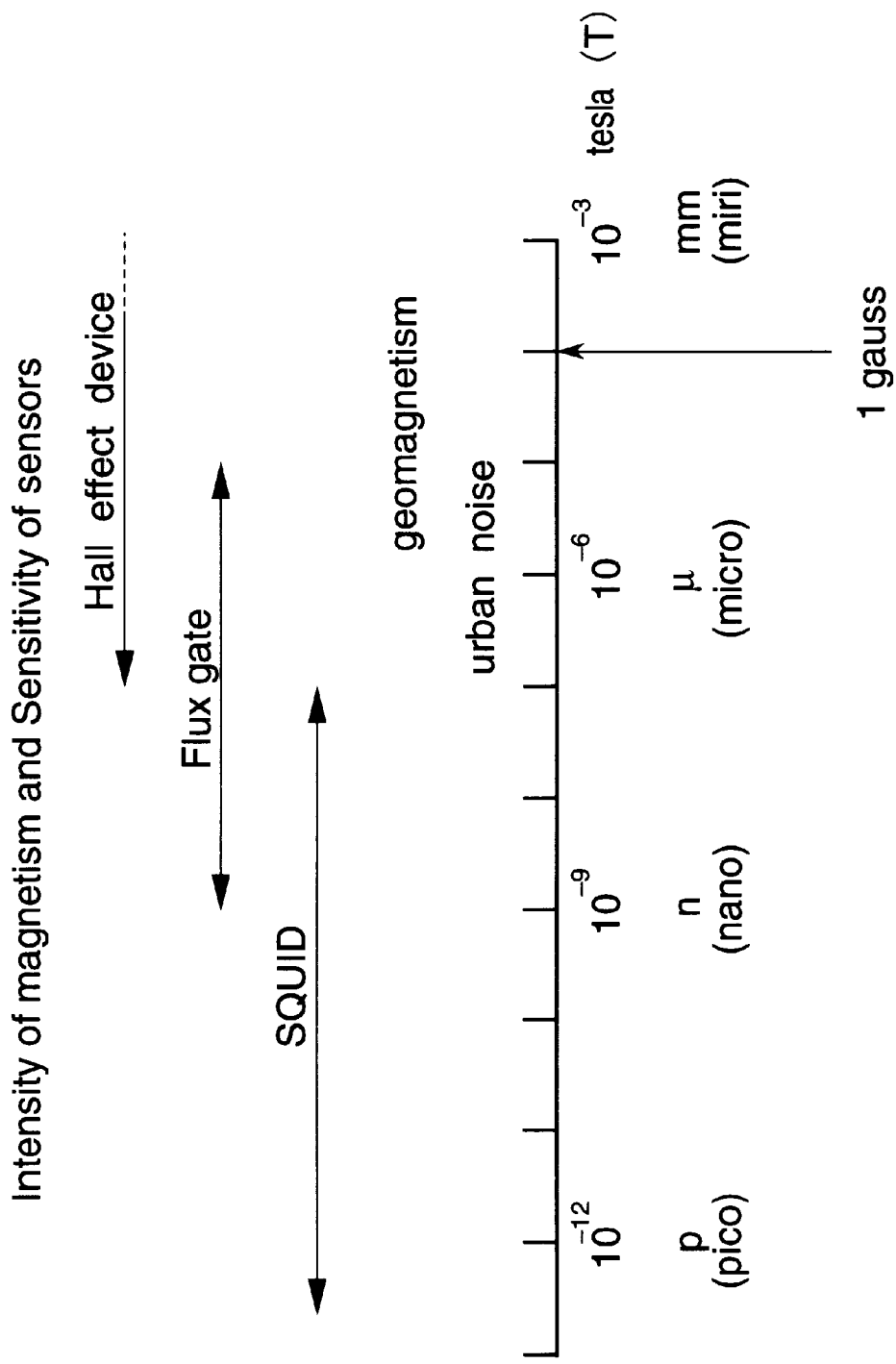
FIG. 2 is a drawing showing sensitivity ranges covered by typical known sensors.

FIG. 2 shows ranges of sensitivity covered by typical known sensors. One can understood from FIG. 2 that a hall effect device which is a typical magnetic sensor is intended to detect relatively stronger magnetic force caused by magnetic materials or iron powder themselves, while, in the present invention, a superconducting quantum interference device (SQUID) of high-sensitivity is used to measure very weak magnetic field which is weaker than terrestrial magnetism and which is caused by a trace of magnetic elements such as ion contained in a substance to be analyze.

Therefore, the density of a trace of magnetic elements such as iron can be determined precisely without any influence caused by outside magnetic noise in a variety of processes on line without delay.

In the method according to the present invention, the concentration of magnetic substances contained in a non-magnetic substance is determined by applying a magnetic field to the non-magnetic substance from outside a duct through which the non-magnetic substance is advanced or conveyed so that magnetic substances contained in the non-magnetic substance are magnetized, and detecting an intensity of magnetic field which is produced substantially only by the magnetized magnetic substance at a downstream in the duct by a magnetic sensor having a superconducting quantum interference device and a signal treating circuit. The superconducting quantum interference device is preferably so-called "high-temperature oxide superconductor SQUID" which permits to reduce the size of apparatus.

In an embodiment of the present invention, the magnetic sensor and parts of duct near to the magnetic sensor are surrounded by a magnetic shield which substantially isolates or cuts outside magnetic noise, so that an intensity produced only from magnetized magnetic substance is detected.

In another embodiment of the present invention, two superconducting quantum interference devices are arranged in the magnetic sensor, a first superconducting quantum interference device is arranged near to the duct, while a second superconducting quantum interference device is arranged far from the duct, and a difference between two outputs is deducted in a differential circuit so as to obtain a detection signal containing substantially no outside magnetic noise.

Figure 3:
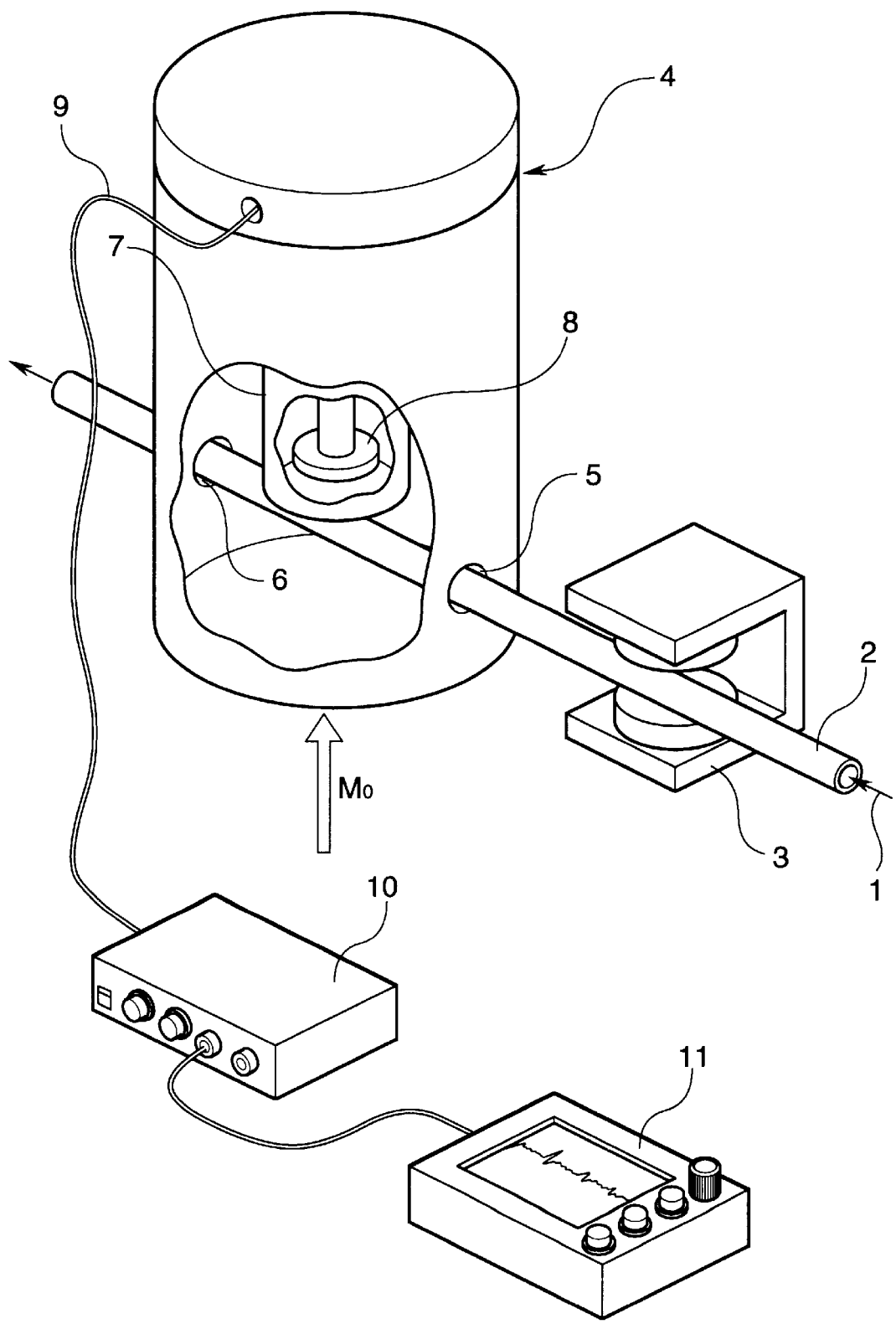
FIG. 3 is a drawing illustrates an apparatus for carrying out the first embodiment of the present invention.

FIG. 3 illustrates an apparatus for carrying out the first embodiment of the present invention. In the present invention, a substance 1 to be analyzed is in a fluid form of liquid or fine powder and is conveyed in a non-magnetic duct or pipe 2. For example, the substance 1 subjected to the mixing and grinding stage A in the process shown in FIG. 1 is fed through the duct 2. The non-magnetic duct 2 can be a plastic pipe having an inner diameter of 3 mm and an outer diameter of 5 mm for example. The duct 2 passes through a means 3 to apply a magnetic field.

The magnetic field applying means 3 which consists of permanent magnets for example magnetize magnetic elements contained in the substance to be analyzed at a predetermined intensity, preferably above an intensity which is higher than the saturated magnetic field of the magnetic elements contained in the substance to be analyzed. The permanent magnets illustrated can be replaced by electromagnets.

Dewar or container 7 arranged at the downstream just after the magnetic field applying means 3 is surrounded by a magnetic shield 4 and is filled with refrigerant such as liquid nitrogen. A magnetic sensor 8 is arranged at the bottom of Dewar 7. The non-magnetic duct 2 passes through holes 5, 6 made on opposite side walls of the magnetic shield 4 and positioned just below Dewar 7 so that the substance to be analyzed can pass very near to the magnetic sensor 8.

In the present invention as the magnetic sensor 8, a superconducting quantum interference device (SQUID) is used. It is preferable to use a superconducting quantum interference device which is made with so-called oxide type "high-temperature superconductor" which can be operated with cheaper liquid nitrogen (−196° C., 77K) which is can be handled easier than liquid helium (−269° C.) which is used in metal type superconducting quantum interference device and which is expensive and can not be handled easily.

The oxide type superconducting quantum interference device can be prepared for example by depositing a thin film of $YBa_2Cu_3O_{7-x}$ or $HoBa_2Cu_3O_{7-x}$ (x=0 to 0.5) on a substrate of $StTiO_3$ by laser evaporation technique. A superconducting junction can be formed by depositing a thin film of superconductor on a step of 0.2 mm height cut on a surface of the substrate. The superconducting quantum interference device has such a high performance that its resolving power is 1/5,0000,000 of terrestrial magnetism so that extremely weak magnetic field can be measured at high sensitivity.

The SQUID magnetic sensor 8 is arranged at the bottom of Dewar 7 filled with liquid nitrogen and the substance to be analyzed conveyed in the non-magnetic duct 2 pass very near to the SQUID magnetic sensor 8, for example at a distance of about 10 mm from the superconducting quantum interference device.

In the first embodiment, Dewar 7 and adjacent part of the duct 2 are surrounded by a magnetic shield 4 made of Permalloy for example which can reduce terrestrial magnetism and environment noise (hereinafter, outside magnetic noise) Mo which is given to the SQUID magnetic sensor 8. At the through-holes 5, 6, the magnetic shield 4 can have cylindrical extensions surrounding parts of the duct 2 outsides the magnetic shield 4 to prevent effectively penetration of outside magnetic noise Mo into magnetic shield 4.

The SQUID magnetic sensor 8 is connected, through a cable 9, to an electric measuring circuit 10 which itself is known and constructs so-called "Flux Locked Loop (FLL)" type sensor circuit with the SQUID magnetic sensor 8. Output of the SQUID magnetic sensor 8 is obtained from a feed-back circuit of its magnetic flux and is fed to an output means 11 which can be any recorder such as a pen recorder or display.

Now, principle function of the first embodiment according to the present invention will be described. In this embodiment, a substance 1 to be analyzed is a solution of silicon nitride ($Si_3N_4$) powder. The solution is for example alcohol solution (concentration of 30 to 50%) containing several ppm to several hundred ppm of iron which is a magnetic element and has a viscosity of 100 to 1,000 CPS (centipoise, cP). This solution is pressurized so as to advance in the non-magnetic duct 2.

The introduced substance 1 to be analyzed is passed firstly through a magnetic field of about 0.1 tesla [T] for example created by a magnetic field applying device 3 consisting of permanent magnets just before measurement, resulting in that magnetic elements contained in the substance 1 to be analyzed are magnetized above a saturation magnetic field.

After the magnetic elements are magnetized in a predetermined intensity of a magnetic field, the substance 1 to be analyzed enter into the magnetic shield 4 to pass near the SQUID sensor 8 at a distance of about 10 mm from the SQUID sensor 8. An output of the superconducting quantum interference device of the SQUID sensor 8 produced by this passage of the substance 1 to be analyzed is detected by the electronics measuring circuit 10 and is obtained as an output voltage Vo from the feed-back circuit. The output voltage Vo is fed to an output means 11 such as a pen recorder which gives the output voltage Vo or corresponding concentration Cf of magnetic substances.

Figure 4:
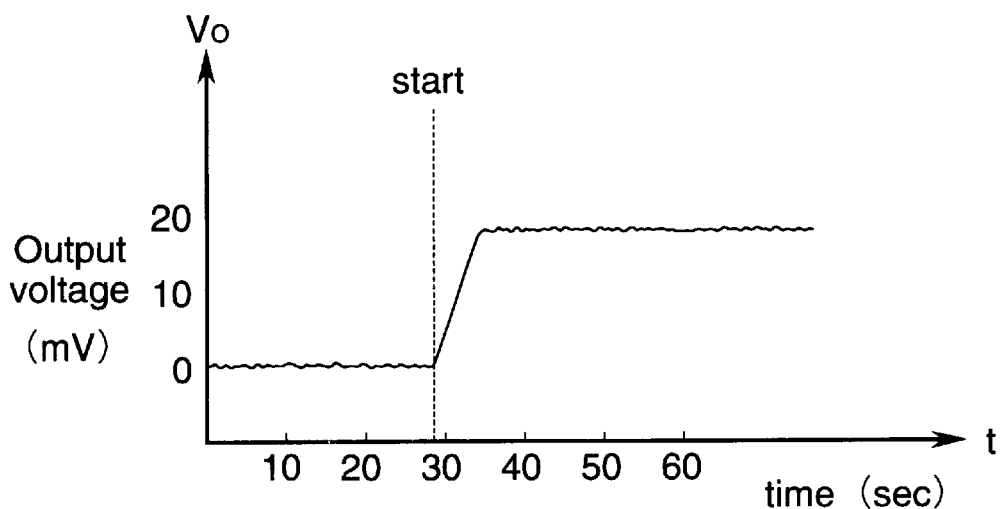
FIG. 4 is a characteristic graph of the output voltage Vo in function of time, obtained by the first embodiment according to the present invention.

FIG. 4 is a characteristic graph of the output voltage Vo in function of time, obtained by the electronics measuring circuit 10 when the substance 1 to be analyzed is liquidated into an alcohol solution (concentration of 40%) of silicon nitride powder containing iron (magnetic substance) at a concentration of 10 ppm and having a viscosity of 500 CPS. As is shown in this drawing, the output voltage Vo starts to elevate when the substance 1 to be analyzed arrive at neighborhood of the superconducting quantum interference device in the SQUID sensor 8, is maintained at nearly constant value until the substance 1 to be analyzed passed away. The output voltage Vo is returned to its initial voltage after completion of passage of the substance 1 to be analyzed.

Figure 5:
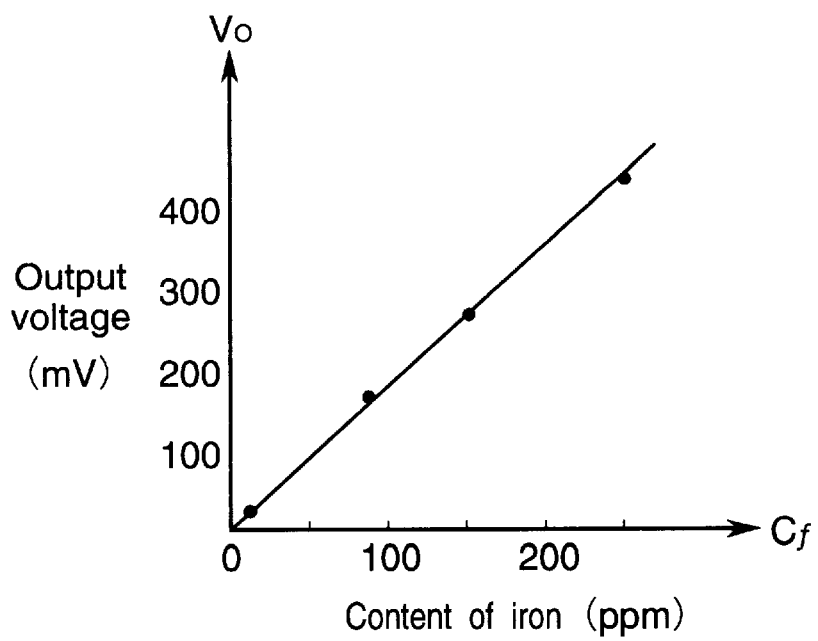
FIG. 5 is a calibration curve showing relationship between the output voltage Vo and the concentration, obtained by the first embodiment according to the present invention.

FIG. 5 is a calibration curve showing a relationship between the output voltage Vo and the concentration Cf of iron contained in a alcohol solution of silicon nitride powder, obtained by using a plurality of substance 1 to be analyzed each containing a different known content of iron (magnetic substance). This graph reveals existence of a linear relation of first order between the output voltage Vo of the superconducting quantum interference device and the concentration of magnetic substances contained in the substance 1 to be analyzed.

Therefore, it is easy to determine the contents of magnetic substances for unknown solution whose concentration of the magnetic substances such as iron is not known by using the linear relation of first order. Still more, since the SQUID magnetic sensor 8 or Dewar 7 and a part of the duct near thereto are surrounded by a magnetic shield 4, terrestrial magnetism and environment outside magnetic noise Mo can be reduced to a negligible level so that a trace of magnetic elements can be detected in very high precision.

As the substance 1 to be analyzed, ten (10) different samples were prepared and their densities of magnetic substances were determined firstly by the SQUID magnetic sensor 8 according to the present invention and then their precise densities were determined by chemical titration. From comparison between the results obtained, it is showed a difference in measurement of ±5% which is considered acceptable in usual applications.

In practice, the output voltage Vo of the SQUID magnetic sensor is measured for a variety of standard solutions whose concentration Cf of magnetic substances is known previously and precisely to prepare a calibration curve or a table showing a relationship between the output voltage Vo of the sensor and the concentration Cf of magnetic substances. The calibration curve or table can be input in the output means 11 in a well-known manner, so that the concentration Cf of magnetic substances in a substance 1 whose concentration Cf of magnetic substances is unknown can be output or displayed in a form of graph or a figure at once when the output voltage Vo of the SQUID magnetic sensor is input. In other words, the results of measurement of the concentration Cf of magnetic substances in unknown substance 1 can be observed immediately.

Figure 6:
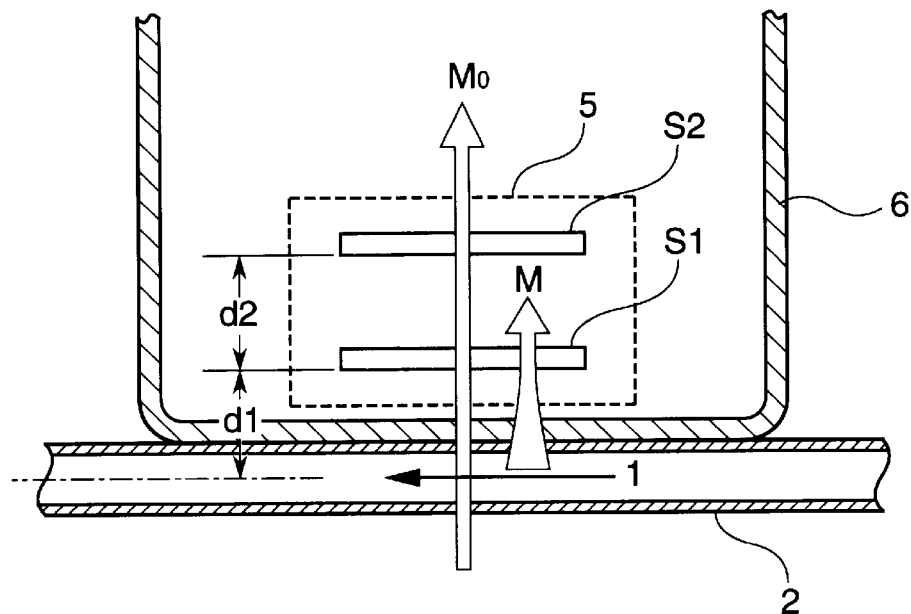
FIG. 6 is an illustration of an arrangement of SQUID magnetic sensor to explain the principle of the second embodiment according to the present invention.

In the second embodiment, the magnetic shield 4 used in the first embodiment is eliminated but the same precise result can be obtained by using two superconducting quantum interference devices. FIG. 6 is an illustration of an arrangement of SQUID magnetic sensor to explain the principle of the second embodiment.

In the second embodiment, the SQUID magnetic sensor is constructed by two superconducting quantum interference devices S1 and S2 which are arranged coaxially at a predetermined distance or clearance d2 in a direction which is perpendicular to the elongated direction of the non-magnetic duct (plastic tube) 2 or a flow direction of the substance 1 to be analyzed. The first superconducting quantum interference device S1 is placed at a distance d1 which is very near to the non-magnetic duct 2 through which the substance 1 to be analyzed flow, for example at a distance of about 10 mm from the non-magnetic duct 2. The distance or space d2 between two superconducting quantum interference devices S1 and S2 is enough long with respect to the distance d1 and is about 100 mm, for example. Outputs of two superconducting quantum interference devices S1 and S2 are fed to the electronics measuring circuit 10.

In the electronics measuring circuit 10, two outputs from two superconducting quantum interference devices S1 and S2 are compared in an operational amplifier and a difference therebetween is determined. The difference is used to reduce the terrestrial magnetism and environment noise Mo to which two superconducting quantum interference devices S1 and S2 are exposed commonly, so as to detect substantially only a signal corresponding to a magnetic field M which is given to the first superconducting quantum interference devices S1 from the substance 1 to be analyzed.

Precisely, the two superconducting quantum interference devices S1 and S2 are exposed or subjected to terrestrial magnetism and environment noise Mo in addition to tile magnetic field M which As given by magnetized substance in the substance 1 to be analyzed. These outside magnetic noise function commonly and equally to two superconducting quantum interference devices S1 and S2. On the other hand, the magnetic field M given by magnetized substance vary according to such a principle that an intensity of magnetic field is in reverse proportional to third power of a distance from an origin or source of the magnetic filed. In fact, an intensity of magnetic filed obtained from the substance 1 to be analyzed in the second superconducting quantum interference device S2 which is located far from the duct is reduced to about third power of a ratio in distance (d1/d2) or about $1/10^3$ and hence become negligible. Therefore, the outside magnetic noise can be canceled by deducting a difference between two outputs from two superconducting quantum interference devices S1 and S2 in the operational amplifier, resulting in that only an output which represents an intensity of a magnetic field M which is given to the first superconducting quantum interference device S1 from the substance 1 to be analyzed.

In this manner, it can be obtained an output in which the outside magnetic noise Mo which is given to two superconducting quantum interference devices S1 and S2 commonly is reduced in the operational amplifier. The output voltage is fed to the an output means 11, in the same manner as the first embodiment, which gives as the result of measurement the output voltage Vo or corresponding concentration Cf of magnetic substances.

In practice, for the same substance to be analyzed as the first embodiment, an equal output voltage was obtained by passing the output signal from the operational amplifier to an amplifier having an amplifying function of 1 to 1,000 times and by fine adjustment. The result showed that a difference in measurement of concentration increased to ±6% which is considered acceptable in usual applications.

It is preferable to design shape and location of apparatus in such a manner that the magnetic field created by magnetized magnetic substances is given to the superconducting quantum interference device as more effective as possible, since the substance to be analyzed contain only a trace of magnetic elements to be detected.

Figure 7:
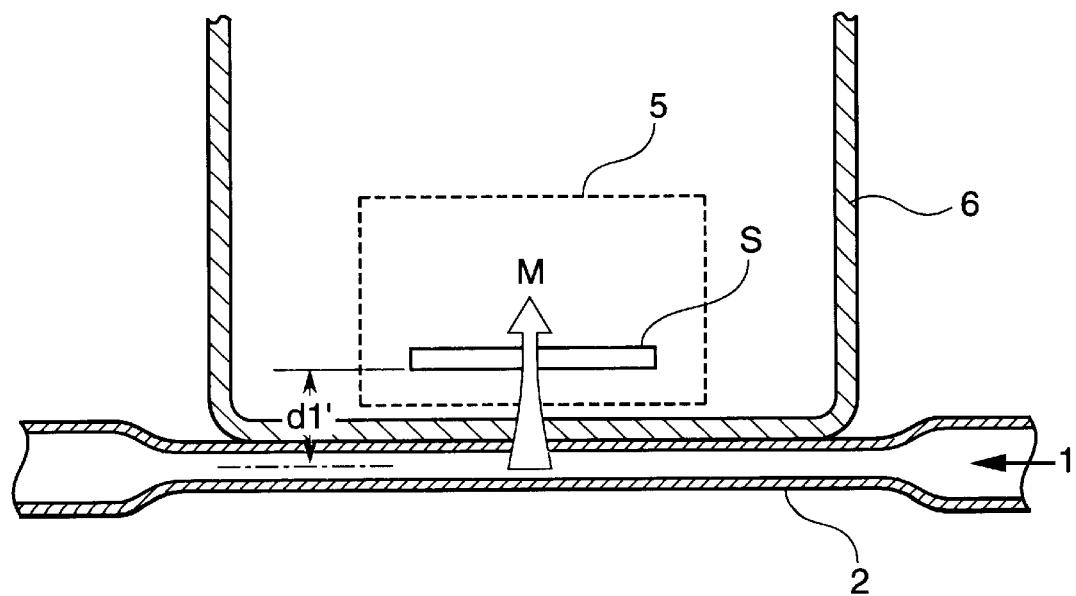
FIG. 7 is a drawing illustrating a variation of the present invention.

In a variation shown in FIG. 7, a part of the duct 2 is flattened at least in the neighborhood of the SQUID magnetic sensor 5. Such flattened duct can reduce a distance d1' between the center of the duct 2 and a superconducting quantum interference device S in the SQUID magnetic sensor 5 (d1'<d1), so that the substance to be analyzed as a whole pass at a nearer position to the superconducting quantum interference device S, resulting in that the magnetic field created by magnetized magnetic substances is given to the superconducting quantum interference effectively A desired flow rate or flow pattern can be obtained by increasing or decreasing a cross section of the duct from a circle or by modifying tapering between the flattened section and circular section.

The present invention permits to determine the density of a trace of magnetic elements contained in a non-magnetic substance by using a superconducting quantum interference device of high sensitivity in such a condition that the terrestrial magnetism and environment noise Mo are reduced in a non-contacting mode and precisely, so that measurement can be effected rapidly on line without delay. In the present invention, data can be obtained continuously so that it can be used as a monitor in a production lines.

We claim:

1. Method for determining concentration of magnetic substances contained in a non-magnetic substance, comprising:
    advancing a non-magnetic substance through a duct;
    applying a magnetic field to said non-magnetic substance from outside said duct so that magnetic substances contained in said non-magnetic substance are magnetized;
    detecting an intensity of magnetic field which is produced substantially only by said magnetized magnetic substance by a magnetic sensor having a superconducting quantum interference device (SQUID) that is located downstream of the point at which said magnetic field is applied; and
    using the intensity of said magnetic field which is produced substantially only by said magnetized magnetic substance to determine the concentration of magnetic substances contained in said non-magnetic substance.

2. The method set forth in claim 1, wherein detection of the intensity of magnetic field is effected in a magnetic shield which surrounds said magnetic sensor and part of said duct near to said magnetic sensor to isolate outside magnetic noise.

3. The method set forth in claim 1, wherein two superconducting quantum interference devices are arranged in said magnetic sensor at different distances from said duct so that outside magnetic noise is substantially eliminated by deducting a difference between two outputs obtained by said superconducting quantum interference devices.

4. The method set forth in claim 1, wherein said superconducting quantum interference device is made of high-temperature oxide superconductor.

5. Apparatus for determining concentration of magnetic substances contained in a non-magnetic substance, comprising a duct made of non-magnetic material through which said non-magnetic substance is advanced, means to apply a magnetic field to said non-magnetic substance from outside of said duct so that magnetic substances contained in said non-magnetic substance are magnetized, means to measure an intensity of magnetic field produced substantially only by said magnetized magnetic substance, including a magnetic sensor having a superconducting quantum interference device means for converting output signals from said magnetic sensor to provide a concentration value for magnetic substances contained in said non-magnetic substance.

6. The apparatus set forth in claim 5, wherein said means to measure the intensity of magnetic field is equipped with a magnetic shield which surrounds said magnetic sensor and part of said duct near to said magnetic sensor to isolate outside magnetic noise.

7. The apparatus set forth in claim 5, wherein said magnetic sensor has two superconducting quantum interference devices, one arranged near to said duct and another arranged far from said duct, and said circuit for treating output signals has a circuit for deducting a difference between two outputs of said superconducting quantum interference devices to obtain detection signals containing substantially no outside magnetic noise.

8. The apparatus set forth in claim 5, wherein said superconducting quantum interference device is made of high-temperature oxide superconductor.

* * * * *